United States Patent
Wang et al.

(10) Patent No.: US 9,037,218 B2
(45) Date of Patent: May 19, 2015

(54) PHOTOACOUSTIC CONTRAST AGENT BASED ACTIVE ULTRASOUND IMAGING

(75) Inventors: Yao Wang, Arlington, VA (US); William Tao Shi, Briarcliff Manor, NY (US)

(73) Assignee: KONINKLIJKE PHILIPS N.V., Eindhoven (NL)

(*) Notice: Subject to any disclaimer, the term of this patent is extended or adjusted under 35 U.S.C. 154(b) by 19 days.

(21) Appl. No.: 13/501,683

(22) PCT Filed: Oct. 11, 2010

(86) PCT No.: PCT/IB2010/054595
§ 371 (c)(1),
(2), (4) Date: Apr. 12, 2012

(87) PCT Pub. No.: WO2011/045734
PCT Pub. Date: Apr. 21, 2011

(65) Prior Publication Data
US 2012/0203103 A1 Aug. 9, 2012

Related U.S. Application Data

(60) Provisional application No. 61/252,214, filed on Oct. 16, 2009.

(51) Int. Cl.
*A61B 8/14* (2006.01)
*A61B 5/00* (2006.01)
*A61B 8/08* (2006.01)

(52) U.S. Cl.
CPC ............... *A61B 5/0095* (2013.01); *A61B 8/481* (2013.01)

(58) Field of Classification Search
CPC ............................... A61B 8/481; A61B 5/0095
USPC ................... 600/431, 437, 443–447, 458, 454
See application file for complete search history.

(56) References Cited

U.S. PATENT DOCUMENTS

| 5,706,819 A | 1/1998 | Hwang |
| 6,095,980 A | 8/2000 | Burns |

(Continued)

FOREIGN PATENT DOCUMENTS

| WO | 2009057021 A2 | 5/2009 |
| WO | 2009072022 A1 | 6/2009 |

OTHER PUBLICATIONS

Egerev, Serger. et al "Acoustic Signals Generated by Laser-Irradiated Metal Nanoparticles" Applied Optics Optical Society of America, vol. 48, No. 7, Mar. 1, 2009.

*Primary Examiner* — Long V Le
*Assistant Examiner* — Angela M Hoffa (57) ABSTRACT

Electromagnetic energy is applied to thereby oscillate a bubble that is then insonified to produce an echo (260) for reception and analysis to afford imaging of the region of the bubble. To create the bubble, the energy may be applied to a nano particle (232) of a contrast agent whose consequent internal nano- or micro-bubbles offer, with novel pulsing techniques, greater sensitivity, and which can permeate outside vasculature (216) prior to being energized thereby affording quantification of vascular permeability and delivery of targeting molecules. The particle can include an absorbing and an evaporating parts, the irradiation (204), as by near-infrared laser, causing the phase change that gives rise to the bubble. The echo may occur in response to ultrasound interrogation (220) of the activated contrast agent, which could entail pulse inversion, power modulation or contrast pulse sequence imaging, with persistence processing. The contrast agent might be mixed with microbubble based ultrasound contrast agent to facilitate the timing of bubble activation.

18 Claims, 6 Drawing Sheets

(56) References Cited

U.S. PATENT DOCUMENTS

| | | |
|---|---|---|
| 6,494,841 B1 | 12/2002 | Thomas |
| 6,508,767 B2 | 1/2003 | Burns |
| 6,548,046 B1 | 4/2003 | Lanza |
| 7,575,738 B2 | 8/2009 | Syud |
| 8,313,773 B2 * | 11/2012 | Kim et al. .................... 424/489 |
| 8,617,522 B2 * | 12/2013 | Sharma et al. ............... 424/9.42 |
| 2005/0273010 A1 * | 12/2005 | Shi et al. ....................... 600/458 |
| 2008/0045865 A1 | 2/2008 | Kislev |
| 2008/0160090 A1 | 7/2008 | Oraevsky |
| 2008/0237028 A1 | 10/2008 | Kislev |
| 2009/0187099 A1 | 7/2009 | Burcher |
| 2009/0227997 A1 * | 9/2009 | Wang et al. ..................... 606/10 |
| 2013/0281848 A1 * | 10/2013 | Shi et al. ....................... 600/431 |

\* cited by examiner

– 1 –
PHOTOACOUSTIC CONTRAST AGENT BASED ACTIVE ULTRASOUND IMAGING

FIELD OF THE INVENTION

The present invention is directed to applying electromagnetic energy for imaging and, more particularly, to energizing a substance serving as an ultrasound contrast agent.

BACKGROUND OF THE INVENTION

Photoacoustic (PA) imaging is a noninvasive imaging technique that may be used in medical environments, e.g., to detect, inter alia, vascular disease, skin abnormalities and some types of cancer. PA imaging generally involves flashing a laser at low energy with a near-infrared wavelength onto a target area or region. Infrared light penetrates relatively deeply into the body. This creates a large radiated area for a more detailed picture. Rapid absorption of laser energy expands the tissue (composed of microscopic absorbers) through transient thermo-elastic expansion. The pulsating expansion creates ultrasonic acoustic waves that can be detected by ultrasound detectors of appropriate sensitivity, e.g., ultrasound transducers. The transducer readings can be processed and interpreted using different mathematical equations/algorithms to create two- or three-dimensional images of the target area, showing the tissue structure via spatial distribution of microscopic absorbers or the flow of a bloodstream carrying the absorbers.

PA imaging is effective in anatomical applications based on its unique contrast mechanism. Typically, each tissue or target region absorbs different amounts of the laser energy, making each different target region or tissue potentially unique from a PA imaging standpoint. For purposes of blood vessel-related imaging, hemoglobin generally exhibits high optical contrast when a near-infrared wavelength is applied. This contributes to the sensitivity of blood vessel imaging with PA techniques, enabling doctors/health care providers to see abnormalities in the skin, vascular disease and cancer which can then be treated directly. PA images can be combined with those from other modalities (e.g., ultrasound) to create highly detailed depictions of the target area with complementing contrast. For example, the generated images may facilitate valuable diagnostics, e.g., allowing clinicians to identify small lesions that may be difficult to pick up using other techniques/technologies.

Recently, there have been developed PA contrast agents whose constituent particles are dimensioned down to the nanometer level and are considerably smaller than the microbubbles used in ultrasound imaging.

A PA contrast agent based on particles of nanometer proportion that can diffuse through blood vessels has been used to endocytose cells outside the vasculature. See U.S. Patent Publication No. 2008/0160090 to Oraevsky et al., entitled "Laser-Activated Nanothermolysis of Cells," (hereinafter referred to as the "'090 publication"), the disclosure of which is incorporated by reference in its entirety.

However, this PA contrast agent and other PA contrast agents based on particles of nanometer dimension currently available and under development suffer from low sensitivity due to their low acoustical emission, owing to their small particle size.

Furthermore, incident optical pulsing is generally out of the reception bandwidth of ultrasound instrumentation and, thus, the optical energy is inefficiently converted into ultrasound signals.

Sufficiently energetic laser irradiation of "'090 publication" nanoparticles sufficiently large, or joined in big enough clusters, can produce surrounding microbubbles which would increase acoustical emission, but emergence of the microbubbles requires energizing to a level that thermomechanically destroys local tissue, in accordance with the tumor ablation function of that technique.

Microbubble-based ultrasound contrast agents offer certain recognized advantages in enhancing regular backscatter signals and generating distinct backscatter signals (e.g., super-harmonics and sub-harmonics of incident ultrasound waves) within the ultrasound receive passband. (See, e.g., Shi W T, Forsberg F, Liu J B, Merritt C R B, Goldberg B B: "*New US media boosts imaging quality*," Diagnostic Imaging Global: Special Supplement, November 2000, pp 8-12.)

However, the relatively large size, i.e., of a microbubble, makes known microbubble-based contrast agents unavailable for measuring vascular parameters, such as permeability.

The use of nano-bubbles—which potentially would overcome the limitations associated with known microbubble-based agents—in ultrasound backscatter imaging has not been realized for several reasons. For example, the lifetime of a nano-bubble is too short for intravenous injection and subsequent human circulation, mainly because of the tremendous surface tension against the shell material in this size range. Additionally, the backscatter cross-section of such nano-bubbles is very small. Since backscatter cross-section is determined by the $6^{th}$ power on scatterer size, a factor of 10 reduction in bubble diameter may lead to a $10^6$ times (60 dB) reduction in backscatter power, which is a diminishing return.

SUMMARY OF THE INVENTION

Firstly, it is observed by the present inventors that existing PA agents were primarily developed for optical purposes and rely on increased optical absorption alone to be effective and operable. To date, insufficient attention has been directed to PA agents that improve upon the conversion of absorbed optical energy to in-band ultrasound signals. This lack of effective conversion functionality is a hindrance to the overall effectiveness and applicability of PA agents and PA imaging techniques.

One or more of the above concerns and shortcomings of the prior art are addressed in commonly-assigned International Patent Publication No. 2009/057021, entitled "Photoacoustic Imaging Contrast Agent and System for Converting Optical Energy to In-Band Acoustic Emission," (hereinafter the "'021 publication") to the present inventors, the disclosure of which is incorporated herein by reference in its entirety. The "'021 publication" reveals PA contrast agents that are optimally tuned for the ultrasonic receive passband of the PA transducer to provide more effective imaging systems. In addition, the contrast agents constituents disclosed therein are sufficiently small to permeate capillary walls and like anatomical structures. This permits an expansion of PA imaging/measurement applications, e.g., to vascular parameters such as permeability. These contrast agents are sufficiently stable for advantageous clinical use, e.g., by intravenous injection and circulatory migration to desired locations/regions.

What is proposed herein utilizes the PA contrast agents disclosed in the "'021 publication," and represents an improvement as to systems and methods.

The present inventors have realized that going beyond passive reception of ultrasound can offer even greater sensitivity and therefore more accurate imaging. The echo from an ultrasound transmit can be utilized, for example, to better distinguish blood flow information from that pertaining to the surrounding tissue such as vascular walls. It can also be used to more reliably identify motion, such as by organs due to the heartbeat or respiration. Ultrasound pulsing methods proposed herein advantageously cater to the relatively small acoustic returns by nano-bubbles and microbubbles produced in accordance with the instant disclosure.

In one aspect of the present invention, electromagnetic energy is applied to thereby oscillate a bubble in a region. The oscillating bubble is insonified to produce an echo for reception and analysis to afford imaging of the region.

In one other aspect, the applying causes a phase change in a particle to thereby create the bubble from its particle.

In a different aspect, the particle comprises an elastic coating.

In a further aspect, the phase change occurs in response to absorption of the energy by the particle.

In yet another aspect, the applying comprises applying the energy to an ultrasound contrast medium based on nanoparticles small enough to pass through a vascular wall thereby creating the bubble in a respective one of the nanoparticles.

In a related version, the applying entails applying energy to oscillate a plurality of bubbles that includes the bubble. The insonifying is performed with low mechanical index.

In yet further aspect, the applying is commenced, and the imaging is performed, at a time at which a portion of inflow of the bubbles into vasculature has permeated outside the vasculature.

In some sub-versions, the imaging at that time is performed with persistence processing.

In some sub-versions, the insonifying is performed according to pulse inversion imaging.

In some sub-versions, the insonifying is performed according to power modulation imaging.

In some sub-versions, the insonifying is performed according to contrast pulse sequence imaging.

In a particular aspect, parameters of a contrast agent are tuned to allow conformance of a power spectrum of bubble oscillation to an ultrasound transducer receive spectral sensitivity curve.

In another, related aspect, inflow of microbubbles into vasculature is detected, and the applying is commenced responsive to the detecting.

In a particular embodiment, the method further includes receiving the echo and analyzing the received echo to afford the imaging.

In some embodiments, the insonifying includes firing a plurality of ultrasound pulses in a common direction, and the analyzing entails coherently combining data echoed back from the pulses.

In other embodiments, the insonifying produces a plurality of echoes that are received, and the analyzing comprises combining signals based on the echoes and analyzing the combined signals.

In another alternative aspect, an ultrasonic device features a transmission activator configured for delivering electromagnetic energy to excite a substance in a region so as to enhance utility of the substance as an ultrasound contrast agent, and for delivering, to the excited substance, ultrasound to afford imaging of the region.

In a related alternative aspect, the delivering of electromagnetic energy includes issuing separate bursts of electromagnetic pulses that propagate to the region and, in accordance with a tunable parameter of the substance, match a frequency of consequent energy absorption by the substance to a target frequency of bubble oscillation in the region by the energy.

In other, further aspects, the substance includes a nanoparticle-based contrast medium comprising a nanoparticle. Delivering electromagnetic energy expands the nanoparticle into a particle that includes a bubble oscillated by the energy, the bubble serving as an interrogation target for the imaging.

According to other different aspects, the ultrasonic device further includes an ultrasound transducer with a spectral sensitivity curve, the exciting being such as would cause by itself, without the delivered ultrasound, emission of an acoustic signal whose power spectrum is overlapped, area-wise, by the curve by more than half.

In some yet further versions, a computer software product for medical analysis incorporates a computer readable storage medium embodying a computer program that includes instructions executable by a processor to perform at least the acts of: applying electromagnetic energy to thereby oscillate a bubble in a region; and insonifying the oscillating bubble to produce an echo for reception and analysis to afford imaging of the region.

In other still further versions, an article of manufacture comprises a machine-accessible storage medium having instructions encoded thereon for enabling a processor to perform medical analysis by executing acts, including: applying electromagnetic energy to thereby oscillate a bubble in a region; and insonifying the oscillating bubble to produce an echo for reception and analysis to afford imaging of the region.

In one, yet, additional aspect, the present disclosure features a mixture of nanoparticle-based contrast agent and microbubble-based ultrasound contrast agent.

Details of the novel, photoacoustic contrast agent based active ultrasound imaging are set forth further below, with the aid of the following drawings, which are not drawn to scale.

DETAILED DESCRIPTION OF EMBODIMENTS

Figure 1:
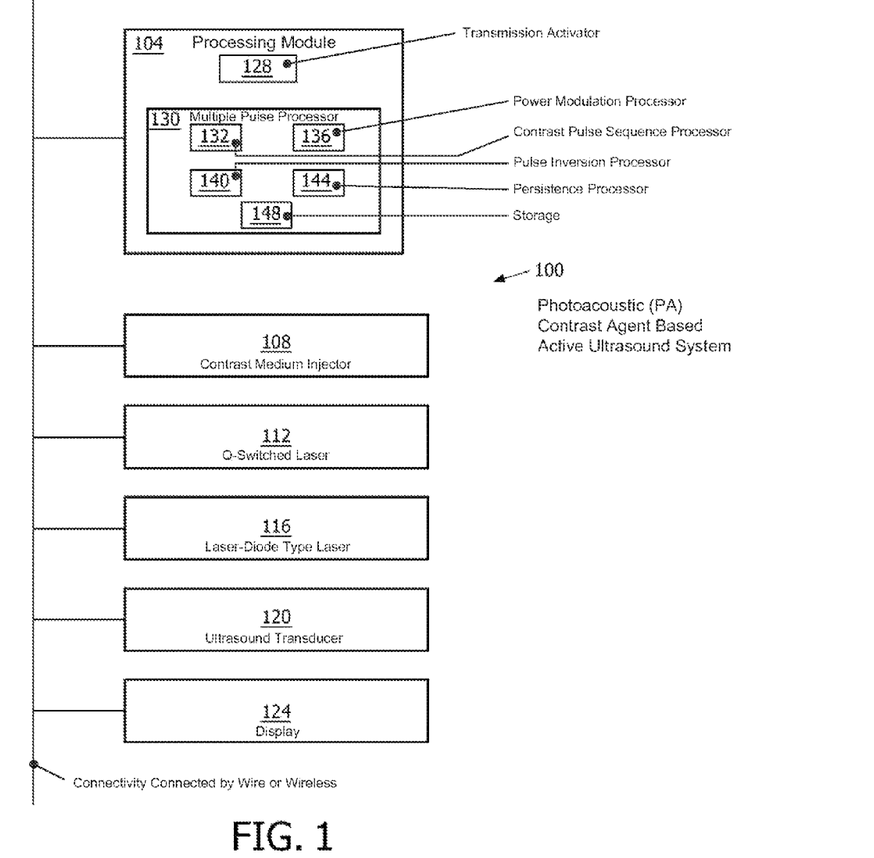
FIG. 1 is a schematic diagram demonstrating, by example, a design for a photoacoustic contrast agent based active ultrasound imaging system.

FIG. 1 offers, by way of illustrative and non-limitative example, a design for a photoacoustic (PA) contrast agent based active ultrasound imaging system 100. The imaging system 100 features a processing module 104, a contrast medium injector 108, a Q-switched laser 112, a laser-diode type laser 116, a transducer 120 and a display 124, the components being communicatively connected by wire or wirelessly. The processing module 104, implementable with one or more integrated circuits and/or computer software for example, includes a transmission activator 128; a multiple pulse processor 130 including but not limited to one or more of a pulse inversion (PI) processor 132, a power modulation (PW) processor 136, and a contrast pulse sequence (CPS) processor 140; a persistence processor 144; and storage 148 that includes working storage and control storage.

Irradiation by the laser 112, 116 is commenced by the transmission activator 128 at the appropriate time to activate in-situ the nanoparticle-based contrast agent. At this time, the activator 128 can further activate the transducer 120 to interrogate oscillating bubbles, whose genesis and oscillating occurs as a result of the pulsed laser irradiation. Alternatively, the ultrasound interrogation 220 can be already ongoing at the onset of laser irradiation.

Figure 2:
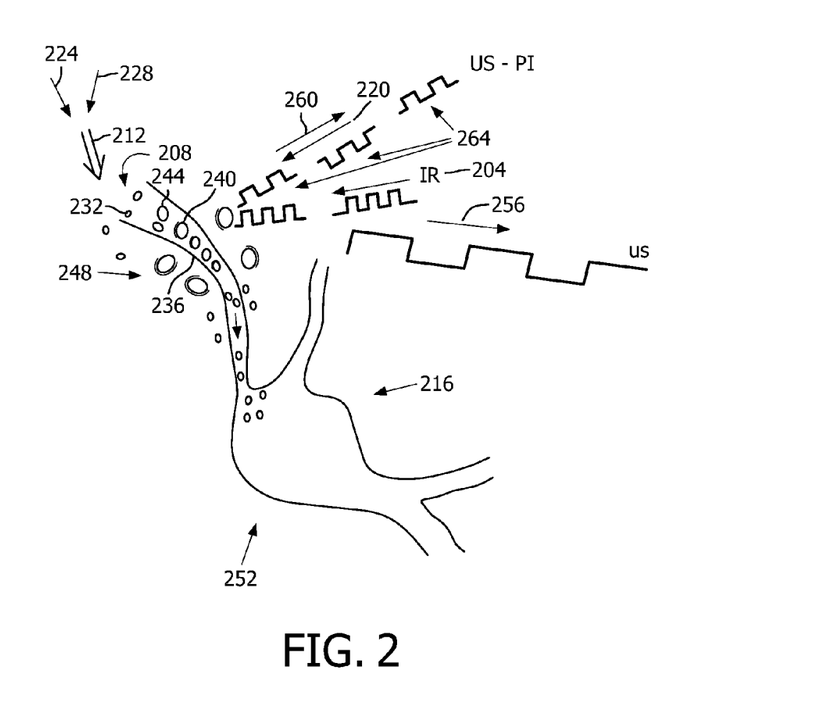
FIG. 2 is a schematic diagram depicting structurally and conceptually an example of an instance of laser irradiation responsive to detection of the inflow of mixed contrast agent into vasculature, and ultrasound interrogation concurrent with the irradiation.

FIG. 2 depicts structurally and conceptually an example of an instance of infrared (IR) or near-infrared laser irradiation 204, by the Q-switched laser 112, responsive to detection of an inflow 208 of mixed contrast agent 212 into vasculature 216. Further depicted is ultrasound interrogation 220, by means of the transducer 120, concurrent with the irradiation.

The mixed contrast agent 212, as originally injected into a subject, e.g., human or animal, in vivo, ex vivo or in vitro, is a mixture in a saline solution, of a nanoparticle-based PA contrast agent 224, as described in the "'021 publication," and any, i.e., typical, microbubble-based ultrasound contrast agent 228. Mixing with the microbubble-based ultrasound contrast agent 228 makes detection of the inflow 208 easier, since irradiation 204 to activate nanoparticles 232 is delayed until the nanoparticles have had a chance to permeate through vasculature walls 236. Once the inflow 208 is detectable, permeation has already occurred or is underway. As mentioned in the "021 publication," selected nanoparticle-based PA contrast agents 224 may be used in combination with conventional microbubble generating media 228 so as to realize the benefits of both contrast agents 224, 228. The mixture 212 may be injected by means of the contrast medium injector 108. Activation of the nanoparticle-based agent 224 is delayed to afford permeation through tissue and blood vessel walls 236, e.g., for purposes of quantifying vascular permeability. The permeation can also serve the molecular imaging/diagnostics purpose of delivering targeting molecules conjugated to the nanoparticles 232.

In the absence of ultrasound interrogation 220, and in the way of background and as discussed in the "'021 publication," the resonance of the nano-bubbles (and/or microbubbles) 240 produced as a result of the near-infrared-irradiation 204 of the nanoparticles is advantageously adapted to function as an efficient acoustic radiator, i.e., an ultrasonic source for purposes of PA imaging systems. (Although its nanoparticle is not shown in FIG. 2, the oscillating bubble 240 is shown with an adjacent contour to represent oscillation, i.e., due to the ongoing, on and off energy absorption of the nanoparticle. It is noted that a microbubble 244 of the microbubble-based medium 228, not having an absorbing part of its own, does not oscillate.)

The novel systems, devices and techniques of the "021 publication" are enhanced by the instant proposal wherein the resonating bubbles 240 serve well as scatterers whose echoes are robustly processed using compatible ultrasound pulsing/imaging techniques afforded by the processing module 104.

Moreover, as seen in FIG. 2, a portion 248 of the inflow 208 that has diffused outside the vasculature 216 has been activated, under the influence of the infrared irradiation 204, to produce oscillating bubbles detectable by means of the interrogating ultrasound 220.

As mentioned in the "021 publication," the laser irradiation 204 is absorbed by an absorbing part of a nanoparticle 232 and thereby heated, typically by only a few degrees Celsius, to cause a part of the nanoparticle to undergo a phase change, i.e., evaporation. This results in a bubble 240, and consequent spatial expansion of its nanoparticle. Pulsed application of the laser 112, 116, and the consequent energy absorption, causes the bubbles 240 that arise to oscillate.

The nanoparticle-based contrast agent/contrast medium 224 may be defined by a nanoparticle 232, e.g., gold nanosphere, nano-rod, or the like, that is encapsulated and/or coated by a coating material. The coating material may be a perfluorocarbon material/composition, with a low boiling point, and is typically optically transparent, while exhibiting mechanical elasticity, thereby allowing the droplet to advantageously expand during phase change.

For delivery purposes, the nanoparticle-based contrast agent/contrast medium 224 may be suspended in a carrier solution, alone or mixed with microbubble-based contrast medium 228, for injection with respect to a target tissue region 252. The carrier solution can be a saline-based solution, such as phosphate buffered saline (PBS). Due to the relatively small size, e.g., between about 50 nm and 500 nm in particle diameter, the medium 224 is free to permeate through capillary walls 236 and the like.

The acoustic signal generated due to bubble oscillation is characterized by a frequency that can be tuned by changing parameters associated with the contrast agent 224, e.g., droplet size, materials of fabrication, coating/encapsulation materials/thickness, properties of multilayered droplets, and the like. The acoustic signals generated are typically characterized by a target frequency or frequency range. The bubbles (e.g., nano-bubbles and/or microbubbles) 232 resonate at frequencies that advantageously match (or substantially match) the spectral sensitivity curve of a receiving ultrasound transducer 120. More particularly, nano-bubble and/or microbubble formation leads to generation of signature PA signals that correspond to the droplet size(s) of the contrast medium 224.

As mentioned above in connection with the instant proposal, the resonating bubbles are actively interrogated by ultrasound pulsing techniques designed to detect and robustly process the small-amplitude oscillations.

Figure 3:
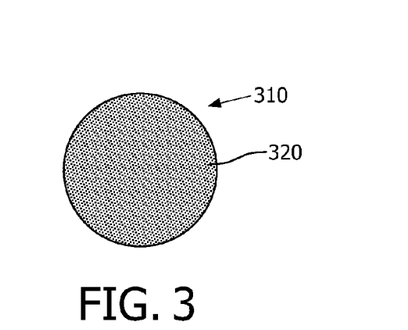
FIG. 3 illustrates an exemplary contrast agent droplet according to the present disclosure.

With reference to FIG. 3 and as disclosed in the "021 publication," a first exemplary embodiment of the nanoparticle-based contrast agent 224 is depicted. The contrast agent 224 is formed of nanoparticle-based droplets 310 of optically absorbing material. The nanoparticle-based droplet 310 is further configured to undergo a phase change, i.e., evaporation, upon absorption of the requisite optical energy, for example laser energy associated with the laser 112, 116. Droplet sizes may vary in the same contrast agent 224 or as between different contrast agents, although the range between 50 nm and 500 nm or a distribution that includes this range is typical.

The nanoparticles 232 that define (in whole or in part) the exemplary droplet 310 of FIG. 3 may take the form of nano-spheres, nano-rods and the like. The nanoparticles 232 are generally optically stimulated by laser energy, thereby generating localized heat that in turn induces a phase change to the droplet 310, i.e., converts the contrast medium 224 from liquid to gas. Such phase change conversion creates nano-bubbles and/or microbubbles. Thus, with further reference to FIG. 3, evaporation occurs inside the spherical droplet 310 once sufficient light is absorbed. Accordingly, the droplet 310 of the first embodiment comprises absorbing and evaporating material 320.

In one example, the absorption cross-section of a gold nanoparticle 232 (e.g., a nano-sphere that is 40 nm in diameter or a nano-rod that is 25 nm in diameter and 100 nm in length) is in the range $10^{-11}$ to $10^{-9}$ cm$^2$. The gold nanoparticle 232 has a volume in the range $10^{-16}$ to $10^{-17}$ cc, a density of 19.3 g/cc and heat capacity of 0.128 J/g° C.

Figure 4:
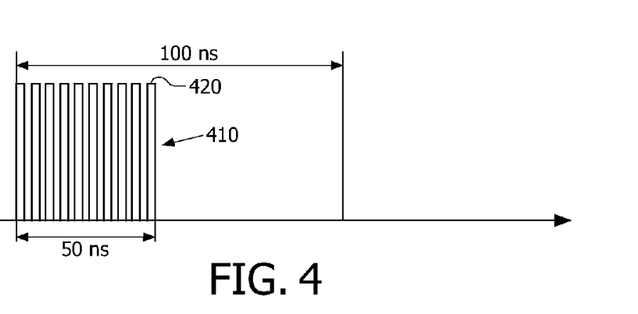
FIG. 4 illustrates an exemplary laser pulse train for use in PA imaging systems of the present disclosure, the pulse train including 50 ns laser irradiation that is made up of 10 individual laser pulses.

FIG. 4 shows an exemplary laser pulse train 410 including 50 ns laser irradiation that includes 10 individual laser pulses 420. Each laser pulse 420 has a temporal duration of 3 ns (e.g., Philips™ Nd:YAG laser source defines this specification). The process may be controlled so that the resultant gas-filled bubbles may resonate at a target frequency, here 10 MHz. The Q-switched laser 112 issues separate bursts 410 of electromagnetic pulses that, in accordance with one or more tunable parameters (e.g., droplet size, materials of fabrication, coating/encapsulation materials/thickness, properties of multi-layered droplets) of the PA contrast medium 224, match a frequency, e.g., 10 MHz, of consequent energy absorption by the medium to a target frequency of bubble oscillation.

Figure 5:
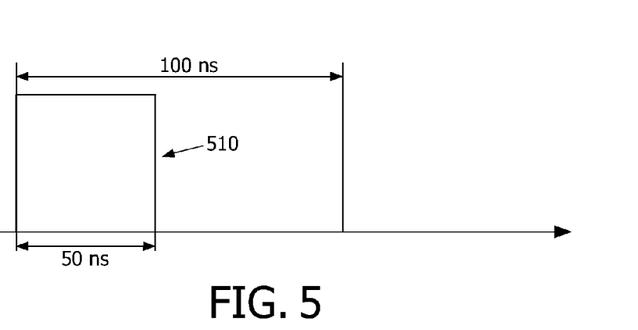
FIG. 5 illustrates an exemplary laser irradiation waveform for use in PA imaging of the present disclosure that represents continuous laser irradiation for 50 ns.

Depending on the optical and thermal diffusivity of a selected material, the actual thermal expansion drive on the contrast agent 224 may resemble a prolonged (approximately 50 ns) impact, as shown in FIG. 5, which can also serve as an exemplary laser irradiation waveform. In an exemplary embodiment, the conversion efficiency can be increased to about 50%. FIG. 5 illustrates a possible laser irradiation waveform representing a single 50 ns pulse 510 of continuous irradiation. This form of excitation may be more easily achieved with the laser-diode type laser 116 of the type commonly used in telecommunications applications. The 50 ns pulse 510 can be repeated at 100 ns intervals as shown in FIG. 6.

Figure 6:
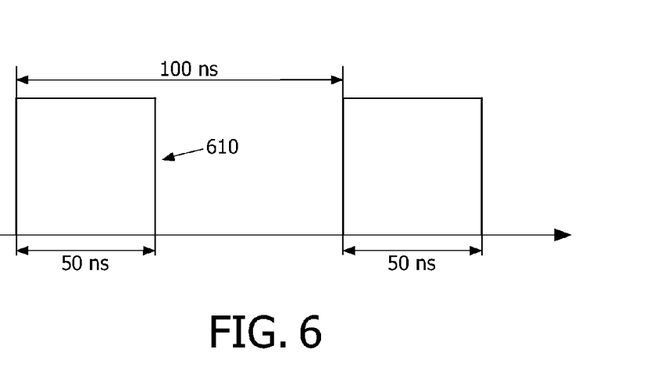
FIG. 6 illustrates an exemplary embodiment of a laser irradiation waveform that advantageously matches the contrast agent response with the bandwidth (or "passband shape") of a PA transducer.

FIG. 6 shows a further laser irradiation waveform that further matches the contrast agent response with the passband shape of the receiving transducer 120. The irradiation waveform of FIG. 6 includes an initial 50 ns laser waveform 610 and one or more repetitions every 100 ns which achieves an upward modulation of the spectrum into the receive spectral sensitivity curve of the transducer 120. The receive spectral sensitivity curve of an ultrasound detector generally resembles a Gaussian or Lorentian shape (with different receiver sensitivities at different frequencies) more than a rectangular window. The waveform excitation associated with FIG. 6 shifts the spectral centroid upward and away from the direct current (DC), thereby achieving an improved coupling in shape.

Figure 7:
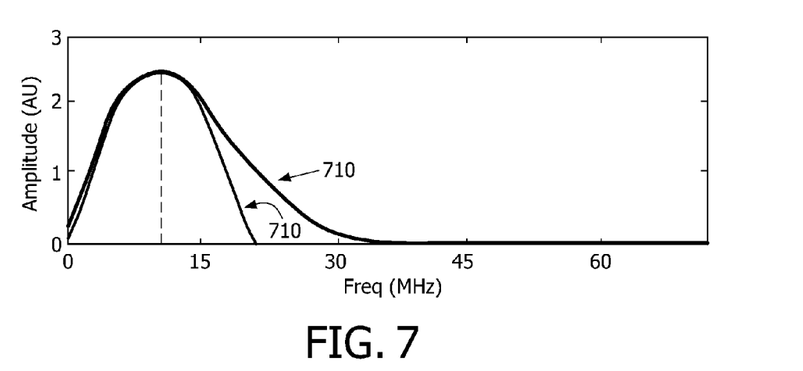
FIG. 7 illustrates, as an example, exciting, by laser irradiation, such as would cause by itself, without the delivered ultrasound, emission of an acoustic signal whose power spectrum is overlapped by the ultrasound transducer spectral sensitivity curve by more than half.

FIG. 7 illustrates, as an example, exciting, by laser irradiation 204, such as would cause by itself, without the delivered ultrasound 220, emission of an acoustic signal 256 whose power spectrum 710 is overlapped, area-wise, by a spectral sensitivity curve 720 of the receive passband of the ultrasound transducer 120 by more than half. Here, in FIG. 7, the overlap is seen to be substantially more than half.

Figure 8:
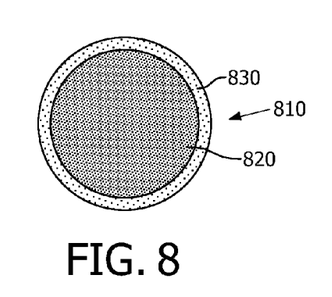
FIG. 8 illustrates an exemplary contrast agent according to the present disclosure that includes a bi-layered nanoparticle with a core of absorbing and evaporating material and an outer shell of an elastic coating material, where, alternatively, the core may be an evaporating material only, while the elastic shell may be an optically absorbing material.

FIG. 8 illustrates an exemplary contrast agent 224 that includes a bi-layered nanoparticle 810 with a core 820 of absorbing and evaporating material and an outer shell 830 of an elastic coating material, where, alternatively, the core may be an evaporating material only, while the elastic shell may be an optically absorbing material. The outer shell 830 avoids the possibility of the nano-bubble or microbubble 240 bursting as a result of the laser irradiation 204. The size and resonant properties/frequency of the nano-bubble/microbubble 240 formed in and by means of the multi-layer/bi-layer nanoparticle 810 of FIG. 8 are akin to those described above with reference to FIG. 3.

Figure 9:
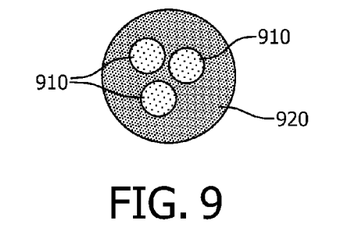
FIG. 9 illustrates an exemplary contrast agent composed of a two-liquid emulsion of nano-droplets, wherein the smaller evaporating droplets are embedded inside a larger droplet.

Another exemplary embodiment is schematically depicted in FIG. 9. Instead of one liquid with both optical absorption and evaporation capabilities (e.g., as in FIG. 3), the exemplary agent 224 of FIG. 9 is an emulsion with two liquids. The emulsion includes at least one evaporating smaller nano-drop 910 inside a larger absorbing nano-drop 920. Two-liquid emulsion droplets can be produced by various techniques, e.g., mechanical stirring, ultrasound sonification, etc.

Figure 10A:
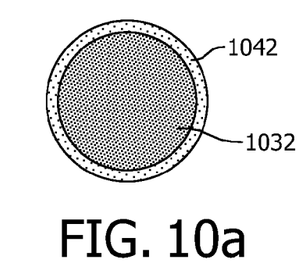
FIGS. 10a, 10b illustrate respectively an exemplary contrast agent made of optically absorbing particles covered with a coating (FIG. 10a) or droplets (FIG. 10b) of evaporating material according to the present disclosure.
Figure 10B:
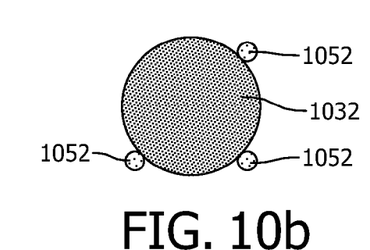

As schematically depicted in FIGS. 10a, 10b, a further exemplary implementation includes an optically absorbing core 1032 (e.g., nano-spheres, nano-rods, etc.) encapsulated or covered with a thin, evaporating, coating material 1042, such as perfluorocarbon chemical(s). The liquid coating 1042 may shrink into tiny droplets 1052 on certain surface pockets (e.g., dents, concave defects and the like) of the core 1032, as seen in FIG. 10b.

Figure 11A:
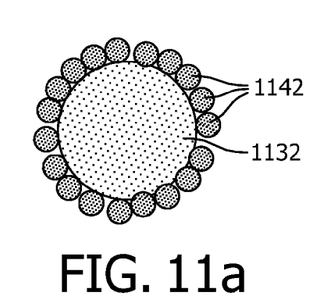
FIGS. 11a, 11b illustrate an exemplary contrast agent consisting of a complex of an evaporation droplet and optically absorbing particles, where in FIG. 11a the evaporation droplet is covered by absorbing particles and, in FIG. 11b, multiple absorbing particles are embedded inside each droplet.
Figure 11B:
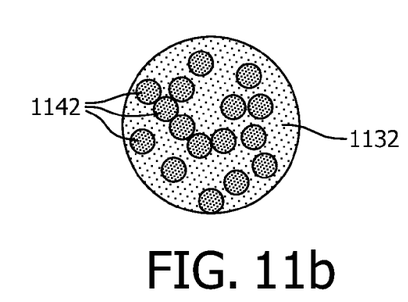

In a further exemplary embodiment, as depicted in FIGS. 11a, 11b, a nanoparticle core 1132 of evaporating material such as perfluorocarbon chemical(s) may be covered by optically absorbing material 1142 such as nano-spheres, nano-rods, etc. Alternatively, the optically absorbing material 1142 may be embedded inside the core 1132 of evaporating material, as seen in FIG. 11b.

It is noted that attachment of absorbing particles to evaporating droplets can be achieved based on various chemical and/or physical interactions, e.g., based on chemical affinity, molecular or biological conjugation, etc. For example, particles can be bound by ligands that are embedded on the surface of droplets. With respect to this type of conjugation, use may be made of a specific technique which is based on an avidin-biotin adhesion, as this conjugation provides an extremely strong non-covalent interaction between a protein and a ligand, with an affinity of $10^{15}$ M$^{-1}$ at pH 5. See Journal of Controlled Release, 2007.

With reference to multi-layer/bi-layer contrast agent embodiments, after phase change/evaporation is effected, a gas-filled nano-bubble or microbubble with a shell of optically transparent material is generally created. The size of the bubble-containing droplets may be on the order of 500 nm to 5000 nm, although the instant disclosure is not limited to these values. In an exemplary embodiment, the nano-bubbles or microbubbles may have a resonant frequency of about 5 to 15 MHz, although the present disclosure is not limited to these figures.

Figure 12:
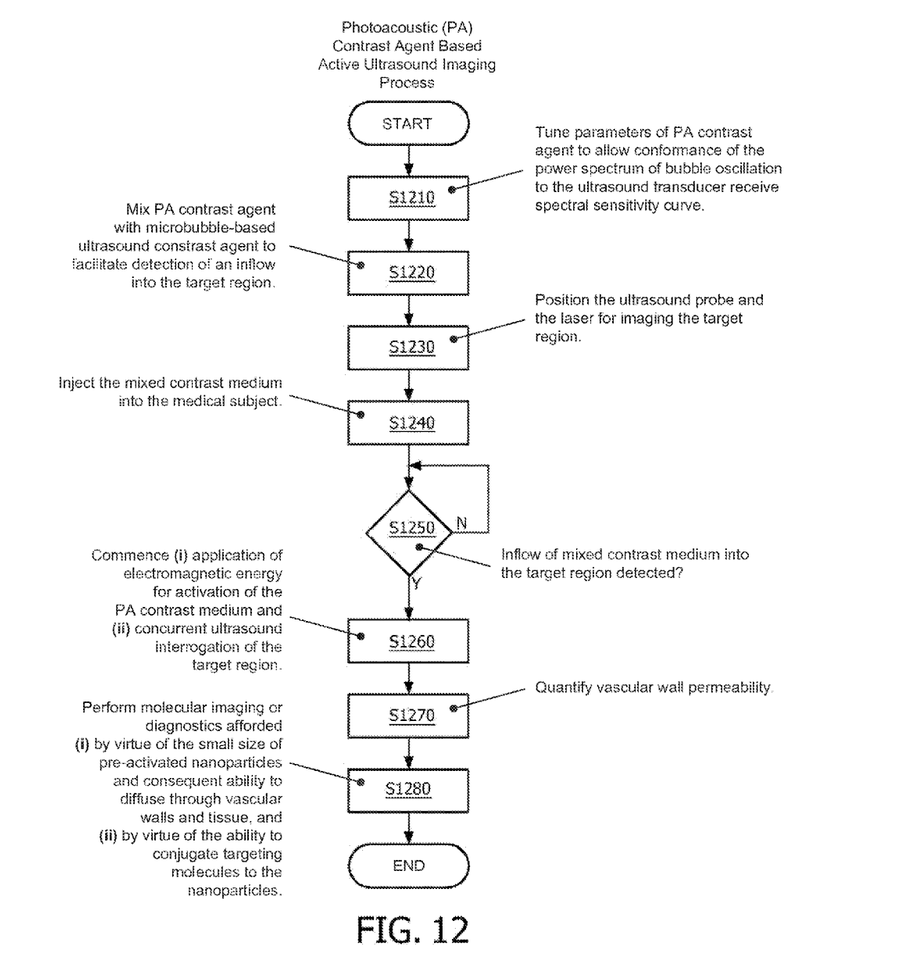
FIG. 12 is a flow chart illustrating an exemplary process of the novel, photoacoustic contrast agent based active ultrasound imaging.

FIG. 12 shows an exemplary process 1200 of the novel, photoacoustic contrast agent based active ultrasound imaging. Parameters of the PA contrast agent 224 are tuned to allow conformance of the power spectrum 710 of bubble oscillation to the ultrasound transducer receive spectral sensitivity curve 720 (step S1210). The PA contrast agent 224 is mixed, in for instance a saline solution, with a microbubble-based ultrasound contrast agent 228 to facilitate detection of the inflow 208 into target vasculature 216. This event is indicative of the occurrence of permeation of the PA agent 224 outside the vasculature (step S1220). The ultrasound probe 120 and the laser 112, 116 are positioned for imaging the target region 252 (step S1230). The mixed contrast medium 212 is injected into the medical subject (step S1240). When the inflow 208 of the mixed contrast medium 212 is detected (step S1250), application of the electromagnetic, i.e., near-infrared laser, energy is commenced. (Laser activation of the PA contrast medium 224 may be performed at a body extremity of the subject, such as an arm or leg, rather than merely at the region 252 of interest to quantify vascular permeability. The laser need not be external, and may be introduced into the body by means of an intravascular applicator or from outside the vasculature.) Concurrent with the laser irradiation 204, ultrasound interrogation 220 of the target region 216 begins, to quantify vascular permeability for example. Low mechanical index (MI) imaging is at low power so that bubble destruction is avoided and non-linear imaging techniques can be used which are particularly sensitive to the low acoustic returns from nano-bubble and microbubble oscillation. Among the low MI, multiple pulse processing techniques usable for ultrasound interrogation 204, in accordance with the instant proposal, is pulse inversion (PI) imaging. This method is described in commonly-assigned U.S. Pat. No. 5,706,819 entitled "Ultrasonic Diagnostic Imaging with Harmonic Contrast Agents," to Hwang et al., hereinafter referred to as the "'819 patent." PI imaging avoids the problem of segmenting the fundamental component of bubble echoes 260 from a harmonic when the fundamental and harmonic overlap. It also alleviates the need for a bandwidth-limited filter. U.S. Pat. No. 6,095,980, entitled "Pulse Inversion Doppler Ultrasonic Diagnostic Imaging," to Burns et al. focuses on accounting for tissue motion in PI imaging, and further discusses the alternative non-linear methods of power modulation (PM) imaging and contrast pulse sequence (CPS) imaging. The latter method is more fully described in U.S. Pat. No. 6,494,841, entitled "Medical Diagnostic Ultrasound System Using Contrast Pulse Sequence Imaging," to Thomas et al. An approach to PI imaging that reduces artifacts and improves sensitivity is found in commonly-owned U.S. Pat. No. 6,508,767, entitled "Ultrasonic Harmonic Image Segmentation," to Burns et al. All of these non-linear techniques emit ultrasound interrogation pulses 264 in a common direction and coherently combine the echoed back data 260. As seen in FIG. 2, the interrogation pulses 264 are on paths that are either coincident, or adjacent and parallel. Adding or subtracting linear combinations of echoed back data 220 from different emitted pulses 264 is an example of coherent combining. The non-linear imaging method is supplemented with persistence processing, which has the effect of delaying a change in a real-time image. The fast attack, slow decay persistence technique is discussed in the "'819 patent" (step S1260). As a result of the ultrasound interrogation 220 and response 260 processed by a non-linear, low MI imaging technique, vascular wall permeability can be quantified (step S1270). At this point, or any time after step S1240, molecular imaging or diagnostics are afforded by virtue of the small size of pre-activated nanoparticles 232 and consequent ability to diffuse through vascular walls and tissue, and by virtue of the ability to conjugate targeting molecules to the nanoparticles (step S1280). Targeted molecular imaging and diagnostics are available, for example, in HerII selectively targeting of breast cancer, see the "'090 publication," $\alpha_v\beta_3$ selectively targeting of endothelium inflammation associated with cardiovascular diseases and rheumatoid arthritis, see U.S. Pat. No. 6,548,046, entitled "Site Specific Binding System, Imaging Compositions and Method," to Lanza et al., and heat shock protein targeting of endothelium transduction, see U.S. Pat. No. 7,575,738, entitled "Heat Shock Protein as a Targeting Agent for Endothelium-Specific In Vivo Transduction," to Syud et al. All of the patents cited above in this paragraph are incorporated herein by reference in their entirety.

Electromagnetic energy is applied to thereby oscillate a bubble that is then insonified to produce an echo for reception and analysis to afford imaging of the region of the bubble. To create the bubble, the energy may be applied to a particle of a contrast agent whose consequent internal nano- or micro-bubbles offer, with novel pulsing techniques, greater sensitivity, and which can permeate outside vasculature prior to being energized thereby affording quantification of vascular permeability and delivery of targeting molecules. The particle can include an absorbing and an evaporating parts, the irradiation, as by near-infrared laser, causing the phase change that gives rise to the bubble. The echo may occur in response to ultrasound interrogation of the activated contrast agent, which could entail pulse inversion, power modulation or contrast pulse sequence imaging, with persistence processing. The contrast agent might be mixed with microbubble based ultrasound contrast agent to facilitate the timing of bubble activation.

It should be noted that the above-mentioned embodiments illustrate rather than limit the invention, and that those skilled in the art will be able to design many alternative embodiments without departing from the scope of the appended claims. For example, as an alternative to mixing the novel PA contrast agent with microbubble based ultrasound contrast agent to aid detection of inflow into vasculature, the inflow timing might be gauged based on empirical data. In the claims, any reference signs placed between parentheses shall not be construed as limiting the claim. Use of the verb "to comprise" and its conjugations does not exclude the presence of elements or steps other than those stated in a claim. The article "a" or "an" preceding an element does not exclude the presence of a plurality of such elements. The invention may be implemented by means of hardware comprising several distinct elements, and by means of a suitably programmed computer having a computer readable storage medium and/or by means of an integrated circuit having a machine-accessible storage medium. The mere fact that certain measures are recited in mutually different dependent claims does not indicate that a combination of these measures cannot be used to advantage.

What is claimed is:

1. A contrast agent based active ultrasound imaging method, comprising:

injecting a contrast agent mixture (i) a nanoparticle-based contrast medium that comprises nanoparticles and (ii) an additional contrast agent into a subject with respect to a vasculature of a target region;

detecting an inflow of the additional contrast agent of the contrast a ent mixture in the vasculature of said target region;

applying pulsed electromagnetic energy to the nanoparticle-based contrast medium located in said target region (i) to cause a phase change in an evaporation part of the nanoparticles that produces bubbles and (ii) to further produce oscillating bubbles (ii)(a) from the bubbles produced by the phase change in the evaporation part of the nanoparticles (ii)(b) in response to an ongoing on and off energy absorption of an absorbing part of the nanoparticles in response to applying the pulsed electromagnetic energy, wherein the oscillating bubbles resonate at a frequency that is detectable by an interrogating ultrasound of an active ultrasound imaging of the vasculature of said target region; and insonifying the oscillating bubbles to produce echoes for reception and analysis by the active ultrasound imaging of the vasculature of said target region, wherein the active ultrasound imaging comprises low mechanical index imaging at low power so that a destruction of the oscillating bubbles is avoided, and wherein (i) said applying of pulsed electromagnetic energy is commenced, and (ii) said low mechanical index imaging is performed, (iii) at a concurrent time in response to (iii) (a) an inflow of the nanoparticle-based contrast medium injected into the subject with respect to the vasculature of said target region being detected via detecting the inflow of the additional contrast agent of the contrast agent mixture in the vasculature of said target region and (iii)(b) for which a portion of the inflow of the nanoparticle-based contrast medium detected in the vasculature of said target region has permeated outside the vasculature of said target region.

2. The method of claim 1, wherein each of the nanoparticles comprises an elastic coating.

3. The method of claim 1, wherein the nanoparticle-based contrast medium further comprises a substance that serves as an ultrasound contrast medium, wherein the nanoparticles of the nanoparticle-based contrast medium are small enough to pass through a vascular wall, and wherein the oscillating bubbles are produced from respective nanoparticles small enough to pass through the vascular wall.

4. The method of claim 1, further wherein said low mechanical index imaging at said concurrent time is supplemented with persistence processing, wherein persistence processing has an effect of delaying a change in a substantially real-time image of said low mechanical index imaging.

5. The method of claim 1, wherein said insonifying is further performed according to pulse inversion imaging.

6. The method of claim 1, wherein said insonifying is further performed according to power modulation imaging.

7. The method of claim 1, wherein said insonifying is further performed according to contrast pulse sequence imaging.

8. The method of claim 1, further comprising:
tuning parameters of the nanoparticle-based contrast medium to enable conformance of (i) a power spectrum of bubble oscillation to (ii) an ultrasound transducer receive spectral sensitivity curve of the active ultrasound imaging.

9. The method of claim 1, wherein the additional contrast agent comprises a microbubble-based ultrasound contrast agent that includes microbubbles,
wherein detecting an inflow of the additional contrast agent of the contrast agent mixture in the vascular of said target region comprises detecting an inflow of the microbubbles of the microbubble-based ultrasound contrast agent in the vasculature of said target region, and wherein applying of pulsed electromagnetic energy to the nanoparticle-based contrast medium is commenced responsive to detecting the inflow of the microbubbles of the microbubble-based ultrasound contrast agent in the vasculature of said target region.

10. The method of claim 1, further comprising:
receiving the echoes; and
analyzing the received echoes via the active ultrasound imaging.

11. The method of claim 10, wherein said insonifying comprises firing a plurality of ultrasound pulses in a common direction, and said analyzing comprises coherently combining data echoed back from the plurality of ultrasound pulses.

12. The method of claim 10, wherein said insonifying produces a plurality of echoes, and said analyzing comprises combining signals based on the plurality of echoes and analyzing the combined signals.

13. A contrast agent based active ultrasonic device comprising:
an ultrasound transducer configured for detecting an inflow of a contrast went mixture having been injected into a subject with respect to a vasculature of a target region, wherein the contrast agent mixture comprises (i) a nanoparticle-based contrast substance that comprises nanoparticles and (ii) an additional contrast agent, further wherein detecting an inflow of the contrast agent mixture in the vasculature of said target region comprises detecting the additional contrast agent of the contrast agent mixture in the vasculature of said target region; and a transmission activator coupled to the ultrasound transducer and a laser the transmission activator configured, via the laser, for delivering pulsed electromagnetic energy to excite the nanoparticle-based contrast substance of the contrast agent mixture having been injected into the subject with respect to the vasculature of said target region so as to enhance utility of said nanoparticle-based contrast substance as an ultrasound contrast agent (i) to cause a phase change in an evaporation part of the nanoparticles that produces bubbles and (ii) to further produce oscillating bubbles (ii)(a) from the bubbles produced by the phase change in the evaporation part of the nanoparticles (ii)(b) in response to an ongoing on and off energy absorption of an absorbing part of the nanoparticles in response to delivering the pulsed electromagnetic energy, wherein the oscillating bubbles resonate at a frequency that is detectable by an interrogating ultrasound of an active ultrasound imaging of the vasculature of said target region, and configured via the ultrasound transducer, for delivering, to the oscillating bubbles, ultrasound to produce echoes for reception and analysis via the active ultrasound imaging of the vasculature of said target region, wherein the active ultrasound imaging comprises low mechanical index imaging at low power so that a destruction of the oscillating bubbles is avoided, and wherein (a) said applying of pulsed electromagnetic energy is commenced, and (b) said low mechanical index imaging is performed, (c) at a concurrent time in response to (c)(1) an inflow of the nanoparticle-based contrast substance injected into the subject with respect to the vasculature of said target region being detected via the ultrasound transducer detecting the inflow of the additional contrast agent of the contrast agent mixture in the vasculature of said target region and (c)(2) for which a portion of the inflow of the nanoparticle-based contrast substance detected in the vasculature of said target region has permeated outside the vasculature of said target region.

14. The device of claim 13, wherein said delivering of pulsed electromagnetic energy comprises issuing separate bursts of electromagnetic pulses that propagate to said target region and, in accordance with a tunable parameter of said nanoparticle-based contrast substance, match a frequency of consequent energy absorption by said nanoparticle-based contrast substance to a target frequency of bubble oscillation in said target region by said pulsed electromagnetic energy.

15. The device of claim 13, wherein said delivering of pulsed electromagnetic energy expands said nanoparticles into particles that include bubbles oscillated by said pulsed electromagnetic energy, wherein said bubbles oscillated by said pulsed electromagnetic energy comprise interrogation targets for said active ultrasound imaging.

16. The device of claim 13, wherein the ultrasound transducer comprises an ultrasound transducer with a spectral sensitivity curve, wherein delivering the pulsed electromagnetic energy causes, without delivered ultrasound, emission of an acoustic signal whose power spectrum is overlapped, area-wise, by said spectral sensitivity curve by more than half.

17. A computer software product for medical analysis with an ultrasound system that includes a processor, an ultrasound transducer and a laser, said product comprising a non-transitory computer readable storage medium embodying a computer program that includes instructions executable by the processor to perform a plurality of acts, said plurality comprising the acts of:
controlling the ultrasound transducer for detecting an inflow of a contrast agent mixture having been injected into a subject with respect to a vasculature of a target region, wherein the contrast agent mixture comprises (i) a nanoparticle-based contrast medium that comprises nanoparticles and (ii) an additional contrast agent, further wherein detecting an inflow of the contrast a ent mixture in the vasculature of said target region comprises detecting the additional contrast agent of the contrast agent mixture in the vasculature of said target region;
controlling the laser for applying pulsed electromagnetic energy to the nanoparticle-based contrast medium of the contrast agent mixture having been injected into the subject with respect to the vasculature of a said target region (i) to cause a phase change in an evaporation part of the nanoparticles that produces bubbles and (ii) to further produce oscillating bubbles (ii)(a) from the bubbles produced by the phase change in the evaporation part of the nanoparticles (ii)(b) in response to an ongoing on and off energy absorption of an absorbing part of the nanoparticles in response to applying the pulsed electromagnetic energy, wherein the oscillating bubbles resonate at a frequency that is detectable by an interrogating ultrasound of an active ultrasound imaging of the vasculature of said target region; and
controlling the ultrasound transducer further for insonifying the oscillating bubbles to produce echoes for reception and analysis by the active ultrasound imaging of the vasculature of said target region, wherein the active ultrasound imaging comprises low mechanical index imaging at low power so that a destruction of oscillating bubbles is avoided, and wherein (i) said applying of pulsed electromagnetic energy is commenced, and (ii) said low mechanical index imaging is performed, (iii) at a concurrent time in response to (iii)(a) an inflow of the nanoparticle-based contrast medium injected into the subject with respect to the vasculature of said target region being detected via the ultrasound transducer detecting the inflow of the additional contrast agent of the contrast agent mixture in the vasculature of said target region and (iii)(b) for which a portion of the inflow of the nanoparticle-based contrast medium detected in the vasculature of said target region has permeated outside the vasculature of said target region.

18. An article of manufacture, comprising a non-transitory machine-accessible storage medium having instructions encoded thereon for enabling a processor of an ultrasound system that also includes an ultrasound transducer and a laser to perform medical analysis by executing acts, including:
controlling the ultrasound transducer for detecting an in of a contrast agent mixture having been injected into a subject with respect to a vasculature of a target region, wherein the contrast agent mixture comprises (i) a nanoparticle-based contrast medium that comprises nanoparticles and (ii) an additional contrast agent, further wherein detecting an inflow of the contrast agent mixture in the vasculature of said target region comprises detecting the additional contrast agent of the contrast agent mixture in the vasculature of said target region;
controlling the laser for applying pulsed electromagnetic energy to the nanoparticle-based contrast medium of the contrast agent mixture having been injected into the subject with respect to the vasculature of said target region (i) to cause a phase change in an evaporation part of the nanoparticles that produces bubbles and (ii) to further produce oscillating bubbles (ii)(a) from the bubbles produced by the phase change in the evaporation part of the nanoparticles (ii)(b) in response to an ongoing on and off energy absorption of an absorbing part of the nanoparticles in response to applying the pulsed electromagnetic energy, wherein the oscillating bubbles resonate at a frequency that is detectable by an interrogating ultrasound of an active ultrasound imaging of the vasculature of said target region; and
controlling the ultrasound transducer further for insonifying the oscillating bubbles to produce echoes for reception and analysis by the active ultrasound imaging of the vasculature of said target region, wherein the active ultrasound imaging comprises low mechanical index imaging at low power so that a destruction of oscillating bubbles is avoided, and wherein (i) said applying of pulsed electromagnetic energy is commenced, and (ii) said low mechanical index imaging is performed, (iii) at a concurrent time in response to (iii)(a) an inflow of the nanoparticle-based contrast medium injected into the subject with respect to the vasculature of said target region being detected via the ultrasound transducer detecting the inflow of the additional contrast agent of the contrast agent mixture in the vasculature of said target region and (iii)(b) for which a portion of the inflow of the nanoparticle-based contrast medium detected in the vasculature of said target region has permeated outside said vasculature of said target region.

* * * * *